US010213199B2

(12) United States Patent
Valiani

(10) Patent No.: US 10,213,199 B2
(45) Date of Patent: Feb. 26, 2019

(54) INTRAORAL STAPLER

(71) Applicant: Shahram Valiani, Downey, CA (US)

(72) Inventor: Shahram Valiani, Downey, CA (US)

( * ) Notice: Subject to any disclaimer, the term of this patent is extended or adjusted under 35 U.S.C. 154(b) by 518 days.

(21) Appl. No.: 14/948,502

(22) Filed: Nov. 23, 2015

(65) Prior Publication Data

US 2017/0143334 A1 May 25, 2017

(51) Int. Cl.
| | |
|---|---|
| *A61B 17/068* | (2006.01) |
| *A61B 17/10* | (2006.01) |
| *A61B 17/064* | (2006.01) |
| *A61B 17/24* | (2006.01) |
| A61B 17/122 | (2006.01) |
| A61B 17/128 | (2006.01) |

(52) U.S. Cl.
CPC ...... *A61B 17/0682* (2013.01); *A61B 17/0644* (2013.01); *A61B 17/24* (2013.01); *A61B 17/128* (2013.01); *A61B 17/1227* (2013.01); *A61B 2017/0645* (2013.01)

(58) Field of Classification Search
CPC . A61B 17/068; A61B 17/105; A61B 17/0682; A61B 17/1227; A61B 2017/0645
USPC .............................. 227/175.1–182.1; 606/219
See application file for complete search history.

(56) References Cited

U.S. PATENT DOCUMENTS

| | | | |
|---|---|---|---|
| 130,853 A | 8/1872 | Hill | |
| 2,881,762 A | 4/1959 | Lowrie | |
| 5,236,440 A | 8/1993 | Hlavacek | |
| 5,289,963 A * | 3/1994 | McGarry | ........... A61B 17/0684 227/175.1 |
| 5,634,932 A * | 6/1997 | Schmidt | ............... A61B 17/122 606/142 |
| 5,862,972 A | 1/1999 | Green et al. | |
| 6,024,748 A | 2/2000 | Manzo et al. | |
| 6,669,073 B2 | 12/2003 | Milliman et al. | |
| 6,953,139 B2 | 10/2005 | Milliman et al. | |
| 7,401,720 B1 | 7/2008 | Durrani | |
| 7,530,484 B1 | 5/2009 | Durrani | |
| 8,870,049 B2 * | 10/2014 | Amid | ............... A61B 17/07207 227/175.1 |
| 2002/0032454 A1 * | 3/2002 | Durgin | ................... A61B 17/10 606/151 |
| 2002/0117534 A1 | 8/2002 | Green et al. | |

* cited by examiner

*Primary Examiner* — Thanh Truong
*Assistant Examiner* — Xavier A Madison
(74) *Attorney, Agent, or Firm* — Argus Intellectual Enterprise; Daniel Enea; Jordan Sworen

(57) ABSTRACT

A surgical stapler configured for intraoral use. The surgical stapler includes an elongated barrel section that allows for surgical staples to be applied to difficult-to-reach locations within a patient's oral cavity. The distal end of the barrel is configured to releasably engage a cartridge containing a plurality of spring-biased surgical staples. When actuated, the surgical stapler ejects a single staple, which slides along a pair of elongated arms extending from the barrel. The distance between the elongated arms increases towards their distal ends, thereby gradually opening the spring-biased staple as it slides therealong until the staple comes to rest within slots on the arms. The user can then place the staple at the wound site and then unhook the arms from the staple. Once free from the arms of the surgical stapler, the staple then closes around the wound site.

13 Claims, 6 Drawing Sheets

INTRAORAL STAPLER

BACKGROUND OF THE INVENTION

The present invention relates to surgical devices. More specifically, the present invention relates to surgical staplers.

Placing oral sutures is a difficult, time-intensive process because many areas of the mouth are difficult to reach. In addition to difficulties associated with reaching wound sites that are situated deep in the oral cavity of a patient, practitioners' movements are often restricted by the mandible and maxilla, forcing them to work at challenging or uncomfortable angles. Despite these difficulties, properly placing oral sutures is critical because sutures ensure proper healing, assist in recovery, and prevent post-surgical complications, such as dry sockets.

SUMMARY OF THE INVENTION

In view of the foregoing disadvantages inherent in the known types of surgical staplers now present in the prior art, the present invention provides a surgical stapler configured for intraoral use. The surgical stapler includes an elongated barrel section that allows for surgical staples to be applied to difficult-to-reach locations within a patient's oral cavity. The distal end of the barrel is configured to releasably engage a cartridge containing a plurality of spring-biased surgical staples. When actuated, the surgical stapler ejects a single staple, which slides along a pair of elongated arms extending from the barrel. The distance between the elongated arms increases towards their distal ends, thereby gradually opening the spring-biased staple as it slides therealong until the staple comes to rest within slots on the arms. The user can then place the staple at the wound site and then unhook the arms from the staple. Once free from the arms of the surgical stapler, the staple then closes around the wound site.

The present invention is designed for intraoral applications, improving the efficiency and convenience of closing wounds within the oral cavities of patients. Furthermore, the present invention ensures that surgical staples are applied in a consistent and reliable manner, reducing the risks associated with improperly closed wounds. Furthermore, the present invention is configured to utilize spring-biased staples that are configured to automatically close around and suture a wound site once applied thereto.

BRIEF DESCRIPTION OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

DETAILED DESCRIPTION OF THE INVENTION

Figure 1:
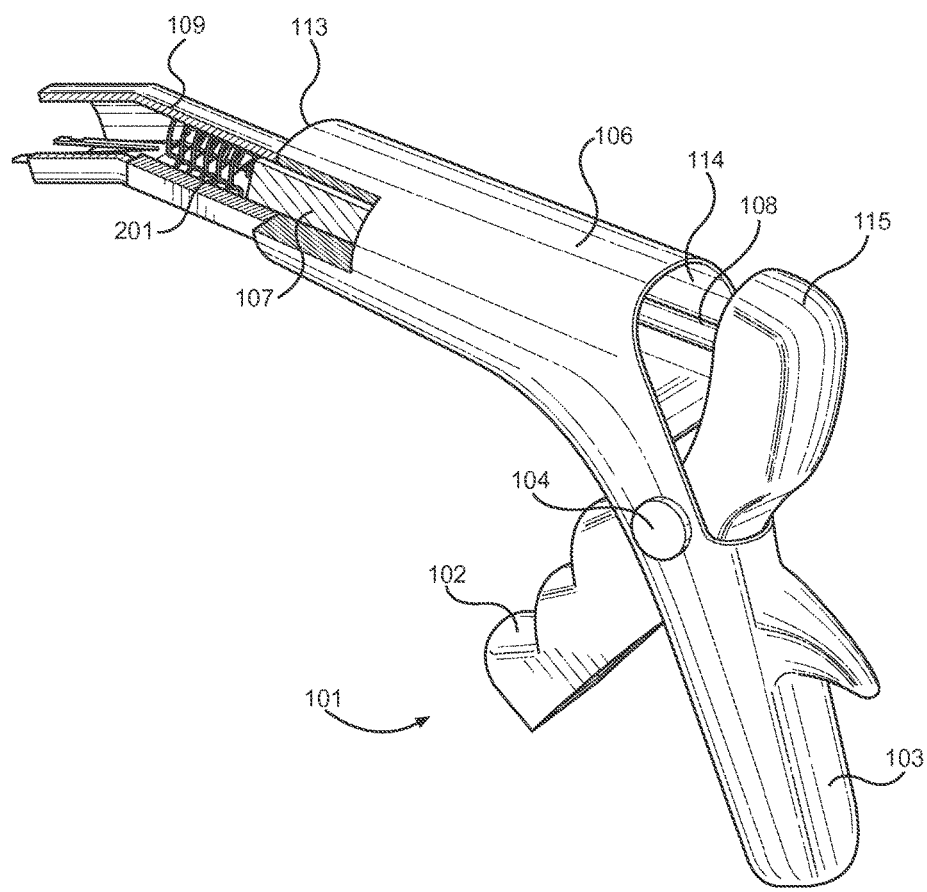
FIG. 1 shows a cutaway perspective view of an embodiment of the stapler.
Figure 2:
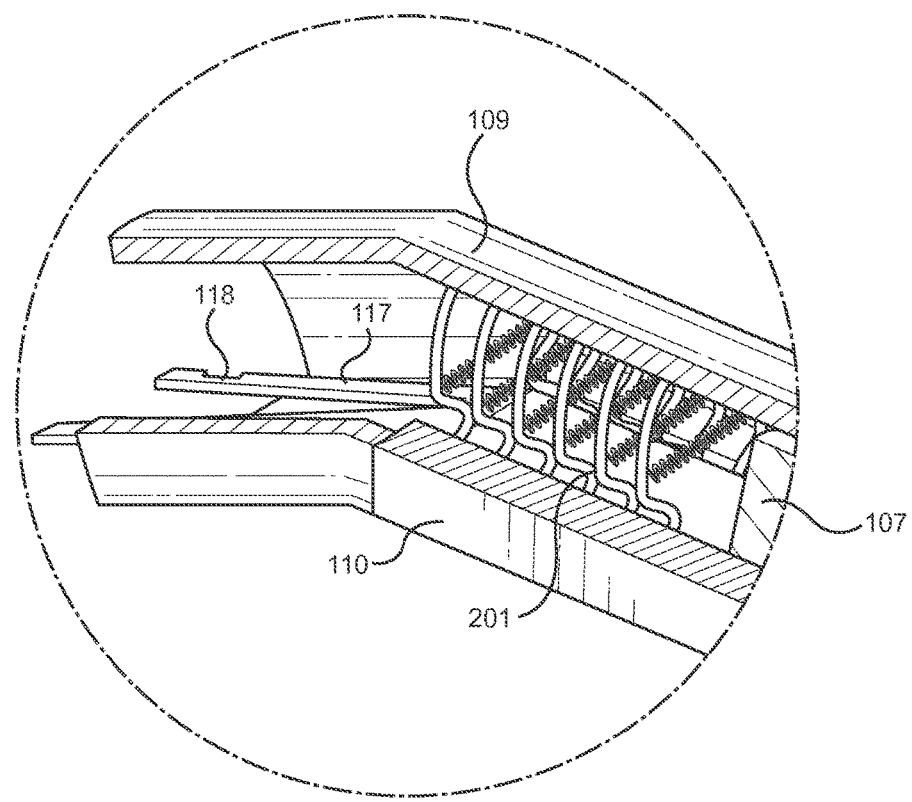
FIG. 2 shows a detail cutaway view of a distal end of a barrel of an embodiment of the stapler.
Figure 3:
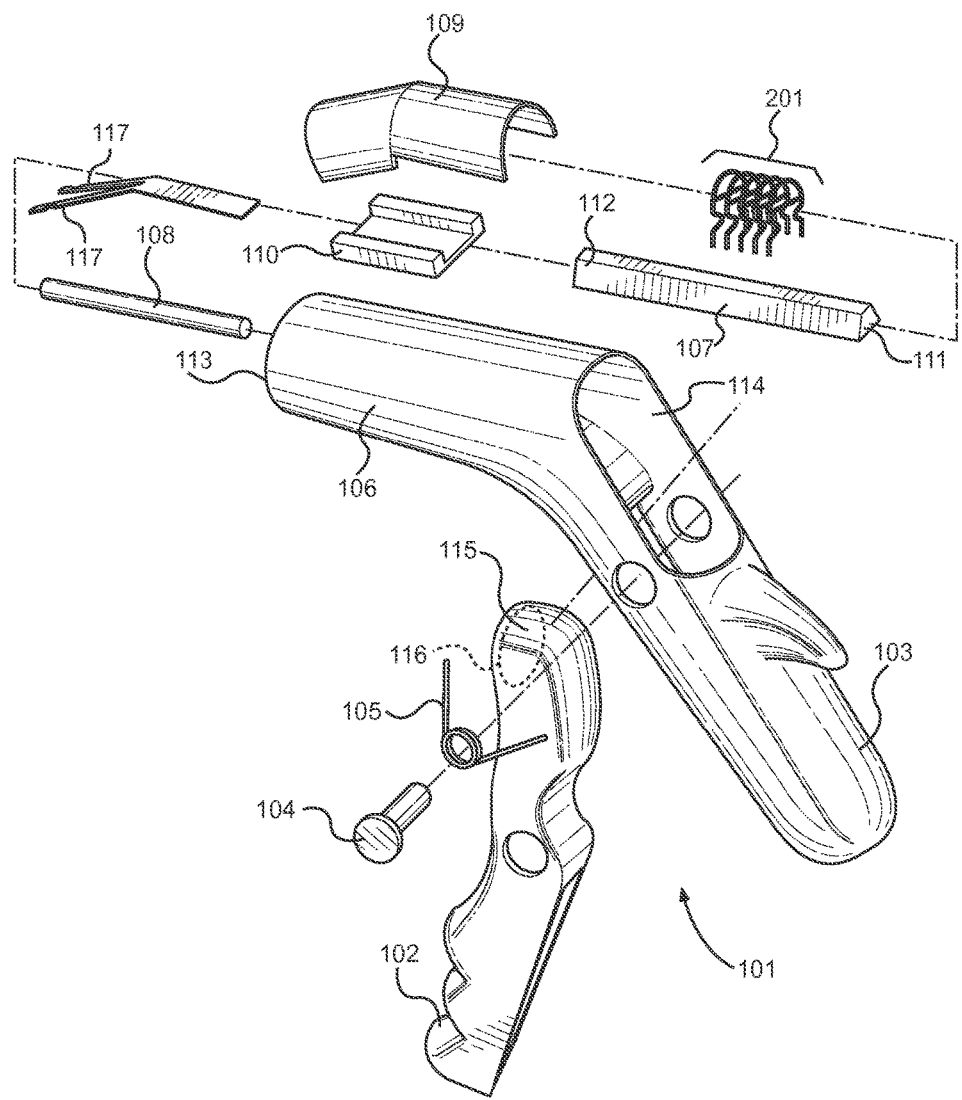
FIG. 3 shows an exploded view of an embodiment of the stapler.
Figure 4:
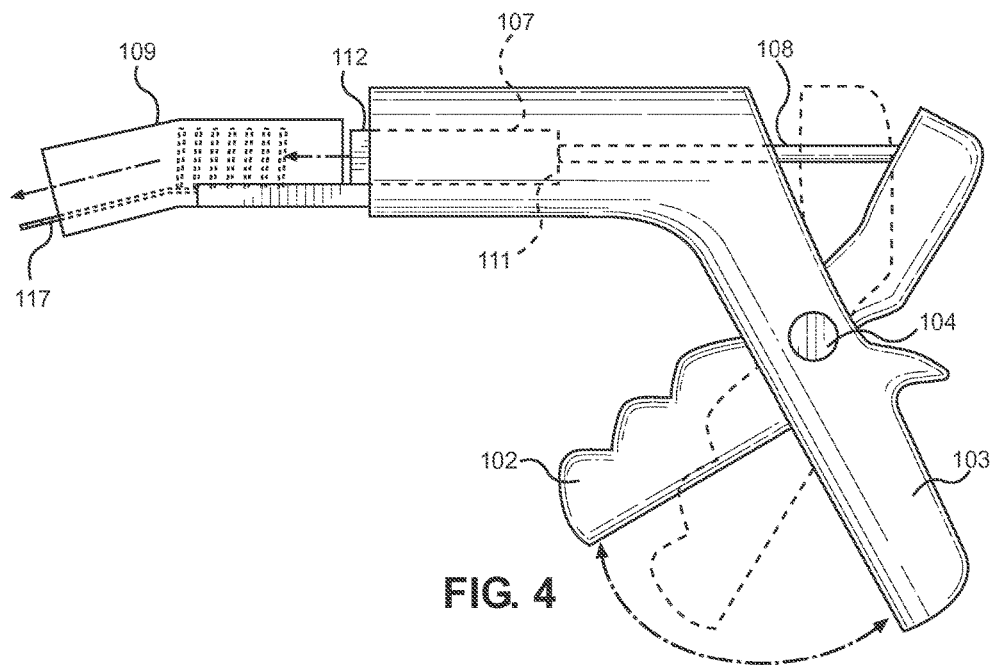
FIG. 4 shows a side profile view of an embodiment of the stapler with the movement of the handle and actuation rod shown in phantom.
Figure 5:
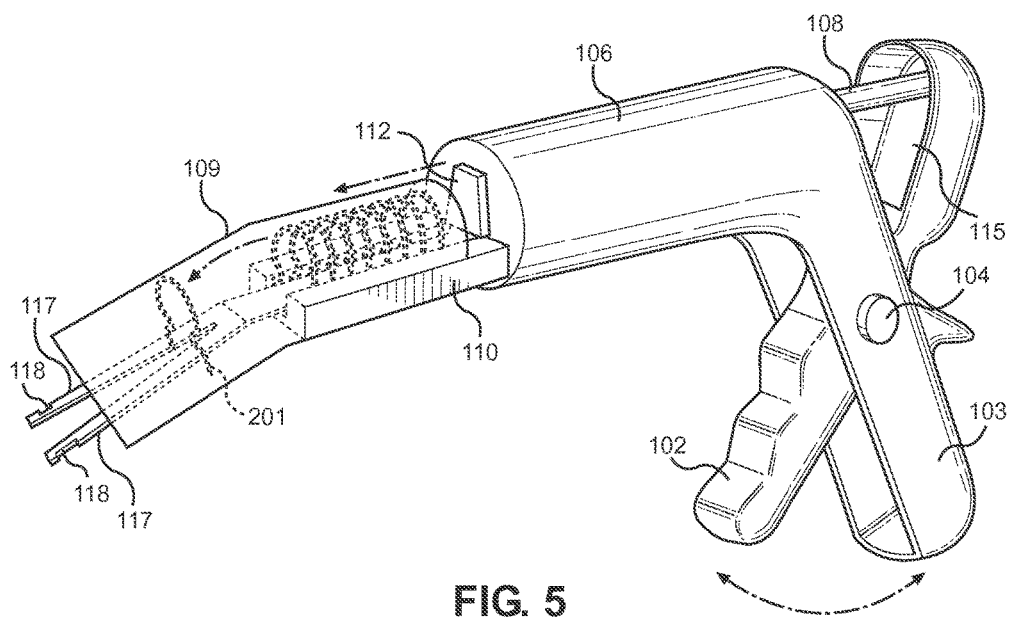
FIG. 5 shows a perspective view of an embodiment of the stapler with the movement of a staple show in phantom.

Reference is made herein to the attached drawings. Like reference numerals are used throughout the drawings to depict like or similar elements of the XXX. The figures are intended for representative purposes only and should not be considered to be limiting in any respect.

Referring now to FIGS. 1-5, there are shown various views of an embodiment of a stapler of the present invention. An illustrative embodiment of the present invention comprises a handle assembly 101 to which a barrel 106 is connected. The handle assembly 101 comprises a movable handle 102 that is attached to a fixed handle 103 via a pivotable connector 104. In the depicted embodiment of the present invention, the barrel 106 and the fixed handle 103 form a single integral structure to which the movable handle 102 is pivotably attached. The barrel 106 comprises an elongated housing that is configured to provide practitioners the requisite length to reach into the oral cavity of a patient and apply staples 201 to wound sites, e.g. the cavities formed via the removal of teeth.

An illustrative embodiment of the stapler further comprises an actuation rod 108 extending from the interior surface 116 of the upper portion 115 of the movable handle 102. Actuation of the movable handle 102 causes the actuation rod 108 move in a linear direction, through the open proximal end 114 of the barrel 106, whereupon it contacts a barrel rod 107 disposed within the barrel 106. The pivotable connector 104 of the handle assembly 101 is configured such that when the movable handle 102 is actuated, the actuation rod 108 is placed into a substantially collinear or aligned position with the barrel rod 107 when it is moved forward to contact the barrel rod 107, thereby causing the distal end of the actuation rod 108 to squarely impact the proximal end 111 of the barrel rod 107. This minimizes the lateral forces exerted on the barrel rod 107 and ensures that the barrel rod 107 travels in a substantially linear direction when contacted.

In one embodiment of the present invention, the handle assembly 101 is configured to automatically return to a resting position once actuated. In the depicted embodiment of the present invention, the handle assembly 101 further comprises a biasing member, e.g. a torsion spring 105, disposed between the fixed handle 103 and the movable handle 102 that is biased to hold the movable handle 102 away from the fixed handle 103. Therefore, when a user releases his or her grip after actuating the movable handle 102, the movable handle 102 automatically returns to its resting position. After returning to its resting position, the movable handle 102 can thereafter be actuated again to eject another one of the staples 202 from the cartridge 201.

In the depicted embodiment of the present invention, the barrel rod 107 is slidably disposed along a track 110 disposed within the interior of the barrel 106 along the longitudinal axis thereof. The track 110 supports the barrel rod 107 as it moves longitudinally. When the proximal end 111 of the barrel rod 107 is contacted by the actuation rod 108, it causes the barrel rod 107 to move in a linear direction through the barrel 106, whereupon the distal end 112 of barrel rod 107 makes contact with a cartridge of staples 201 positioned at the distal end 113 of the barrel 106. The staples 201 are generally aligned with the longitudinal axis of the barrel 106.

The stapler further comprises a pair of arm members 117 extending from the distal end 113 of the barrel 106 along which one or more of the staples 201 are positionable. The distance between the arm members 117 increases from their proximal ends, which are in contact with the barrel 106, to their distal ends, creating a substantially V-shaped configuration for the arm members 117. The V-shape of the arm members 117 causes the staples 201 to gradually open as they slide therealong until they come to rest with a pair of complementary slots 118 disposed at the distal ends of the arm members 117. Once an ejected staple 201 is at rest within the slots 118 at the distal ends of the arm members 117, the staple 201 is held there in place, ready to be applied to a wound site.

One embodiment of the present invention further comprises a cover 109 positioned over the arm members 117. The cover 109 houses the staples 201 resting on the arm members 117, protecting the staples 201 from being jostled or dislodged while the stapler is in use. The cover 109 can be integral to the stapler or removably attachable via any means known in the prior art, e.g., via snap connectors or press-fit.

In one embodiment of the present invention, the barrel rod 107 slidably disposed within the interior of the barrel 106 without restriction to its longitudinal movement. In another embodiment of the present invention, the interior channel of the barrel 106 along which the barrel rod 107 is slidably disposed comprises a ratcheting mechanism that only allows the barrel rod 107 to move towards the distal end 112 in discrete movements and preventing the barrel rod 107 from backsliding within the barrel 106.

Figure 6:
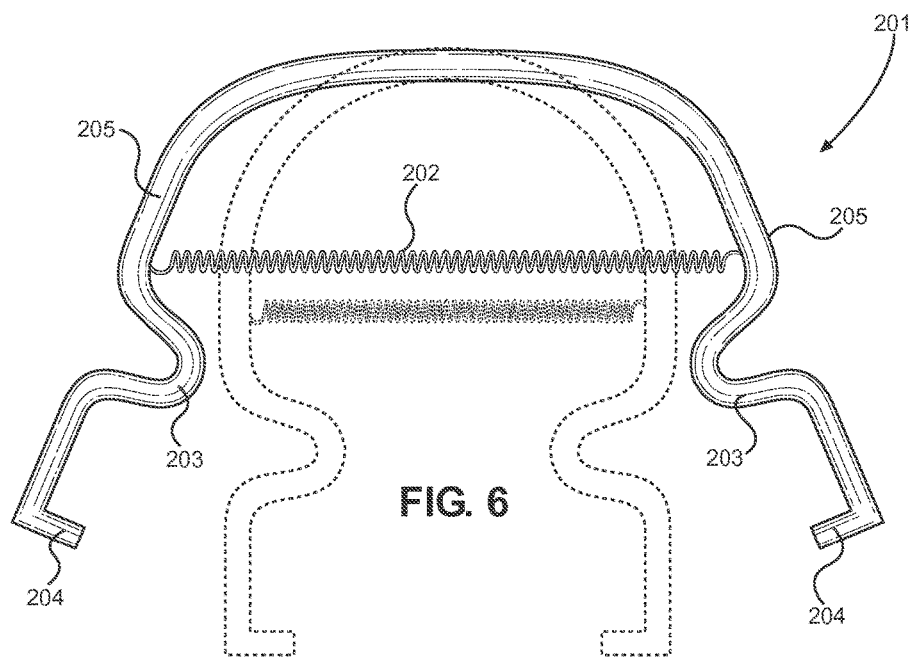
FIG. 6 shows a perspective view of an embodiment of the staple with the movement of the arms shown in phantom.
Figure 7:
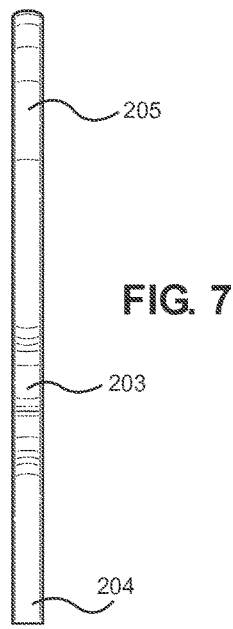
FIG. 7 shows a side profile view of an embodiment of the staple.

Referring now to FIGS. 6 and 7, there are shown views of an embodiment of a staple of the present invention. The staples 201 are configured to work in conjunction with the stapler described herein. In the depicted embodiment, the staple 201 comprises a pair of arm members 205 connected by a spring 202 extending therebetween. The arm members 205 are flexibly connected together such that they can transition between an open position (shown in solid lines) and a closed position (shown in phantom); however, the arm members 205 are also biased towards the closed position in which the arm members 205 are roughly parallel in relation to each other.

Each arm member 205 further comprises an in-turned protrusion 203 disposed at a midpoint thereof and an in-turned flange 204 disposed at the distal end thereof. Both the protrusions 203 and the flanges 204 are directed inwardly so as to grip the flesh around the wound site when the arm members 205 close. The protrusions 203 and the flanges 204 are arranged in a parallel relationship to each other. In the depicted embodiment of the present invention, the protrusions 203 are U-shaped bends in the arm member 205. The flanges 204 are blunted members extending perpendicularly from the distal ends of each of the arm members 205; however, in alternative embodiments, the flanges 204 are pointed in order to assist in gripping the flesh of a patient when utilized to suture a wound site.

In alternative embodiments of the staple 201, the arm members 105 are not connected by a spring 202 extending therebetween. Rather, the staple 201 is constructed from a material that is flexible, yet resilient enough to resist bending and return the arm members 205 to the closed position when opened.

Figure 8:
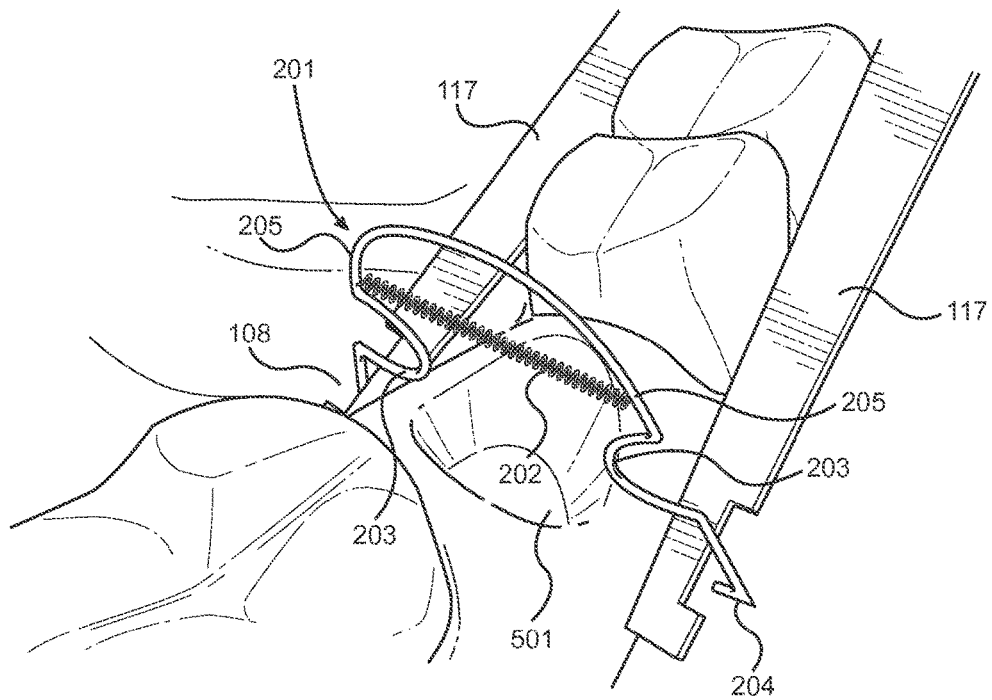
FIG. 8 shows a perspective view of the stapler being used to apply a staple to a wound site.

Referring now to FIG. 8, there is shown a perspective view of the stapler being used to apply a staple to a wound site. When a staple 201 has been ejected and is positioned within the slots 118 disposed at the distal ends of the arm members 117, the staple 201 is ready to be applied to a wound site 501. The user can then position the distal ends of the arm member 117 so that the arm members 205 of the staple 201 are positioned around the wound site 501. The elongated nature of the arm members 205, in combination with the elongated barrel of the stapler, allows for the staple 201 to be applied at any point within the oral cavity of the patient in a convenient manner.

Once the staple 201 is positioned over the wound site 501, the user can then move the stapler so that the arm members 205 are angled downwardly, pulling the protrusions 203 of the staple 201 over the sides of the wound site 501. The staple 201 can be pulled across the wound site 501 via the slots 118 in which the staple 201 is resting pulling against the flange 204 as the arm members 117 are angled downwardly. Pulling the protrusions 203 over the sides of the wound site 501 causes the protrusions to press against the flesh therearound, further widening or opening the arm members 205. This further opening of the arm members 205 allows for the arm members 117 to be disengaged from the staple 201. Once disengaged, the biasing of the staple 201 causes the arm members 205 to close, suturing the wound site 501 closed via pressure from the protrusions 203 and the flanges 204 thereagainst.

Figure 9:
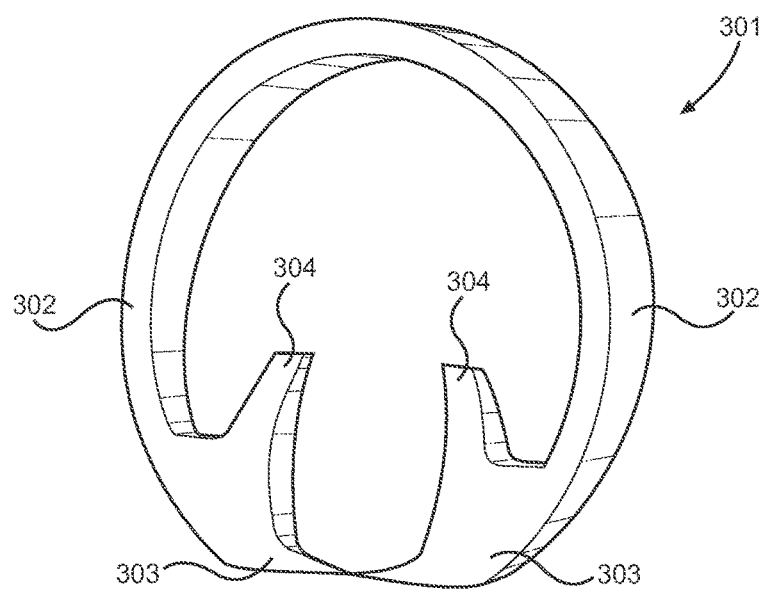
FIG. 9 shows a perspective view of an alternative embodiment of the staple.

Referring now to FIG. 9, there is shown a perspective view of an alternative embodiment of the staple. In this alternative embodiment, the staple 301 comprises a pair of biased arm members 302 arranged in a semi-circular configuration, a pair of pointed ends 303 disposed at the distal ends of the arm members 302, and a pair of in-turned protrusions 304 extending inwardly from a point along the length of the arm members 302. The pointed ends 303 and the protrusions 304 are arranged in a generally perpendicular relationship to each other. When the staple 301 is in its closed position, as depicted, the pointed ends 303 of the staple 301 are in contact, forming a closed loop.

It is therefore submitted that the instant invention has been shown and described in various embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A surgical stapler, comprising:
   a barrel extending from a handle assembly, the barrel having a channel extending therethrough, the channel configured to house a staple therein;
   the handle assembly configured to advance the staple distally towards a first end of the barrel;

the staple configured to be disposed within a gap in a resting configuration, the gap formed between a track and the barrel, wherein the gap is formed on opposing sides of the channel of the barrel, the track extending longitudinally along a length of the barrel;

wherein a flange of the staple is configured to be positioned within the gap, the staple configured to slide along the track upon via actuation of the handle assembly;

a pair of arms extending from the first end of the barrel, the pair of arms being continuous with the track such that the staple being advanced remains therein until selectively ejected;

wherein the hair of arms are configured to prepare the staple for attaching by bearing against the flange to bias the staple to a closed position as the staple advances along the pair of arms;

each arm of the pair of arms comprise a slot on a lateral side thereof, the slot adapted transition the staple to an ejected configuration.

2. The surgical stapler of claim 1, wherein the handle assembly is biased to return to a resting position after being actuated.

3. The surgical stapler of claim 1, further comprising a cover disposed over the arm members, the cover configured to enclose the staple and prevent external contact therewith.

4. The surgical stapler of claim 1, further comprising a slot disposed at a distal end of each of the pair of arm members, the slot configured to receive the staple therein.

5. The surgical stapler of claim 1, wherein the actuation rod extends from an interior surface of the movable handle.

6. The surgical stapler of claim 1, wherein the actuation rod is linearly aligned with the barrel rod when the actuation rod makes contact therewith.

7. The surgical staple of claim 1, wherein the staple comprises a plurality of staples vertically mounted staples in a horizontal feed arrangement.

8. A surgical staple, comprising:
a first arm member;
a second arm member;
wherein the first arm member and the second arm member are spring-biased and symmetrically mirrored about a central axis that bisects the first arm and the second arm;
a protrusion extending inwardly from a midpoint of each of the first arm member and the second arm member;
a flange extending inwardly from a distal end of each of the first arm member and the second arm member;
wherein the distal end are free ends that forms an open gap therebetween, the open gap is configured to receive a wound site;
wherein the flange is configured to contact opposing sides of the wound site and bear the opposing sides towards each other.

9. The surgical staple of claim 8, further comprising a spring extending between the first arm member and the second arm member.

10. The surgical staple of claim 9, wherein the spring is biased to draw the first arm member and the second arm member together.

11. The surgical staple of claim 8, wherein the flange is pointed.

12. The surgical staple of claim 8, wherein the flange of the first arm member and the flange of the second arm member contact each other when the surgical staple is in a closed position.

13. The surgical staple of claim 8, wherein the protrusion comprises a semi-circular bend in each of the first arm member and the second arm member.

* * * * *